United States Patent
Muddasani et al.

(10) Patent No.: US 11,091,470 B2
(45) Date of Patent: Aug. 17, 2021

(54) PROCESS FOR THE PREPARATION OF N-(3-ETHYNYLPHENYL)-7-METHOXY-6-(3-MORPHOLINOPROPOXY) QUINAZOLIN-4-AMINE DIHYDROCHLORIDE

(71) Applicant: NATCO PHARMA LIMITED, Hyderabad (IN)

(72) Inventors: Pulla Reddy Muddasani, Hyderabad (IN); Shankar Reddy Budideti, Hyderabad (IN); Srinivasa Krishna Murthy Konduri, Hyderabad (IN); Nagalingam Samatham, Hyderabad (IN); Venkaiah Chowdary Nannapaneni, Hyderabad (IN)

(73) Assignee: NATCO PHARMA LIMITED, Hyderabad (IN)

( * ) Notice: Subject to any disclaimer, the term of this patent is extended or adjusted under 35 U.S.C. 154(b) by 0 days.

(21) Appl. No.: 16/604,552

(22) PCT Filed: Jun. 19, 2017

(86) PCT No.: PCT/IN2017/050245
§ 371 (c)(1),
(2) Date: Oct. 10, 2019

(87) PCT Pub. No.: WO2018/189747
PCT Pub. Date: Oct. 18, 2018

(65) Prior Publication Data
US 2020/0331899 A1 Oct. 22, 2020

(30) Foreign Application Priority Data
Apr. 15, 2017 (IN) .............................. 201741013419

(51) Int. Cl.
*C07D 413/12* (2006.01)
(52) U.S. Cl.
CPC .................. *C07D 413/12* (2013.01)
(58) Field of Classification Search
None
See application file for complete search history.

(56) References Cited

U.S. PATENT DOCUMENTS

2011/0028473 A1  2/2011  Adibhatla Kali Satya et al.

FOREIGN PATENT DOCUMENTS

| CN | 106432202 A | 2/2017 |
| WO | 2005/070909 A1 | 8/2005 |
| WO | 2009/090661 A1 | 7/2009 |

OTHER PUBLICATIONS

International Search Report issued in connection with corresponding International Application No. PCT/IN2017/050245, dated Jan. 24, 2018, 2 pages.
Chandregowda, Venkateshappa et al., "Synthesis and in vitro antitumor activities of novel 4-anilinoquinazoline derivatives," (Jul. 2009) European Journal of Medicinal Chemistry, 44 (7), pp. 3046-3055.
Cheng, Weiyan et al., Design, synthesis and biological evaluation of 6-(nitroimidazole-1H-alkyloxyl)-4-anilinoquinazolines as efficient EGFR inhibitors exerting cytotoxic effects both under normoxia and hypoxia (Jan. 7, 2015) European Journal of Medicinal Chemistry, 89, pp. 826-834.

*Primary Examiner* — Paul V Ward
(74) *Attorney, Agent, or Firm* — Kilpatrick Townsend & Stockton LLP

(57) ABSTRACT

Present invention relates to an improved process for the preparation of N—(3-ethynylphenyl)-7-methoxy-6-(3-morpholinopropoxy) quinazolin-4-amine dihydrochloride of formula-I.

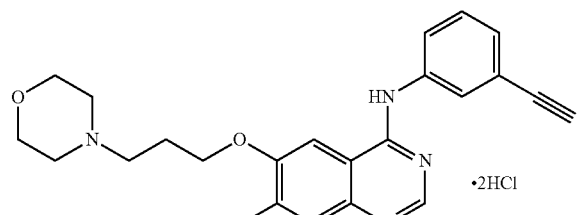

9 Claims, 2 Drawing Sheets

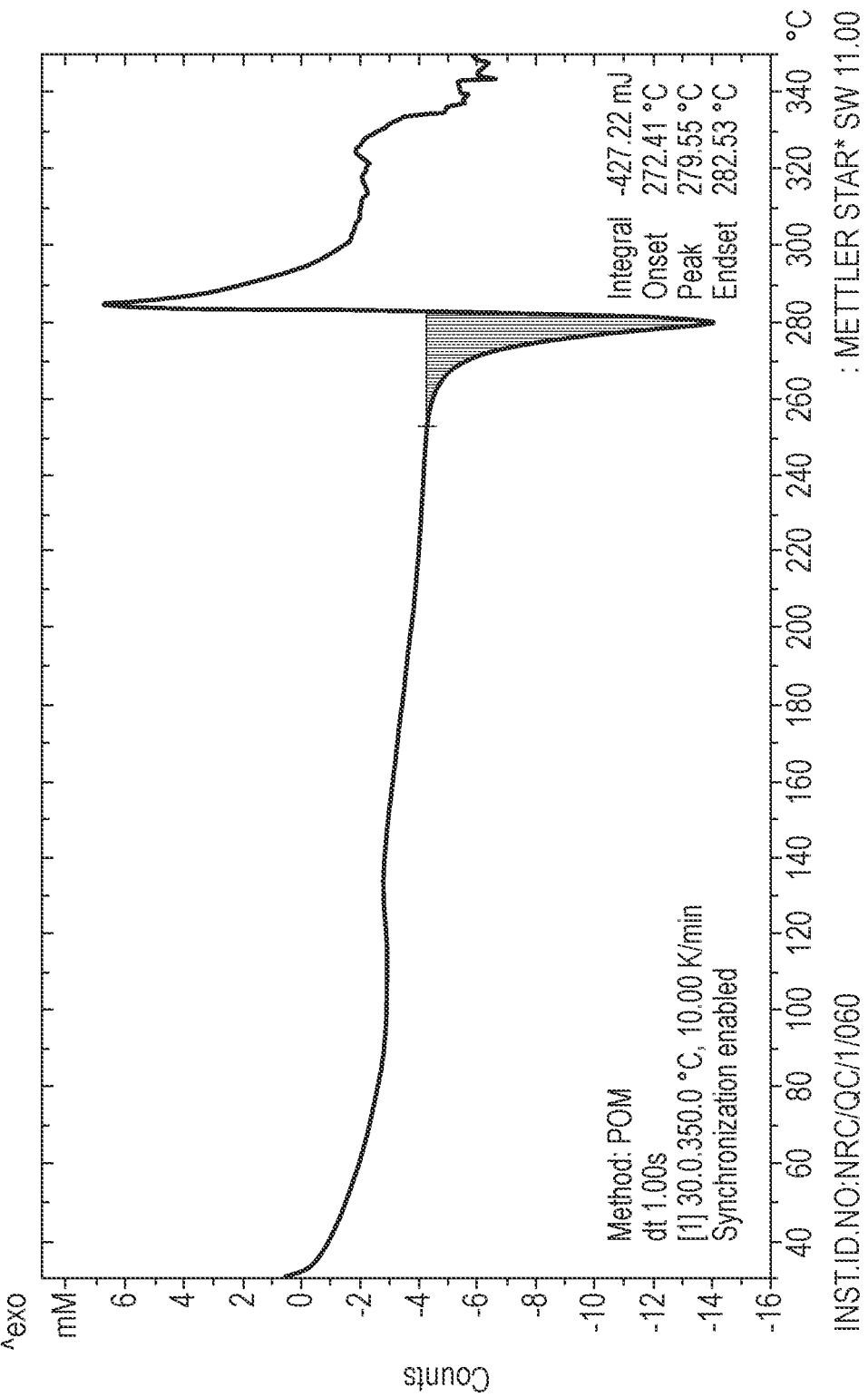
Fig. 2 Differential scanning calorimetry (DSC) of N-(3-ethynylphenyl)-7-methoxy-6-(3-morpholinopropoxy)quinazolin-4-amine dihydrochloride of formula-I.

PROCESS FOR THE PREPARATION OF N-(3-ETHYNYLPHENYL)-7-METHOXY-6-(3-MORPHOLINOPROPOXY) QUINAZOLIN-4-AMINE DIHYDROCHLORIDE

FIELD OF THE INVENTION

Present invention relates to an improved process for the preparation of N—(3-ethynylphenyl)7-methoxy-6-(3-morpholinopropoxy) quinazolin-4-amine dihydrochloride of formula-I.

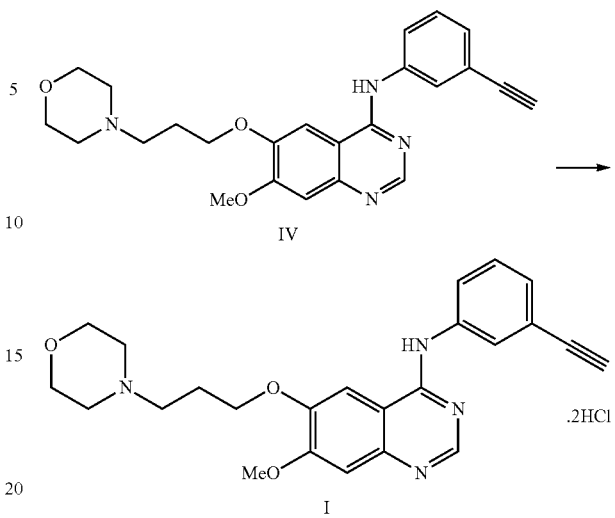

BACKGROUND OF THE INVENTION

The compound of formula-I is an organic small molecule having IUPAC name N—(3-ethynylphenyl)-7-methoxy-6-(3-morpholinopropoxy) quinazolin-4-amine dihydrochloride. It is described in PCT publication number WO2009090661A1, and is described as an inhibitory effect against EGF-type receptor tyrosine kinase enzymes, inhibitory effect against Erb group receptors like Erb-2, Erb-3, and Erb-4 tyrosine kinase sensitive cancers.

Compound of formula-I is therefore being studied in phase I and II clinical trials for HER2 positive breast cancer, drug resistant non-small cell lung cancer.

In WO2009090661A1, compound of formula-I, as shown in scheme-1 is prepared by reacting compound of formula-II with chlorinating agent to get the compound of formula-IIA and is further reacted with 3-ethynylaniline of formula-III to get the compound of formula-IV. Compound of formula-IV is converted to its corresponding hydrochloride salt of formula-I.

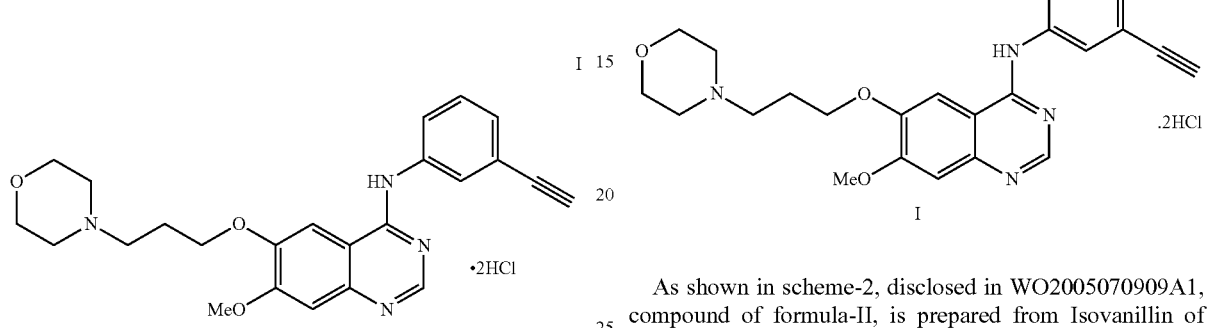

As shown in scheme-2, disclosed in WO2005070909A1, compound of formula-II, is prepared from Isovanillin of formula-V.

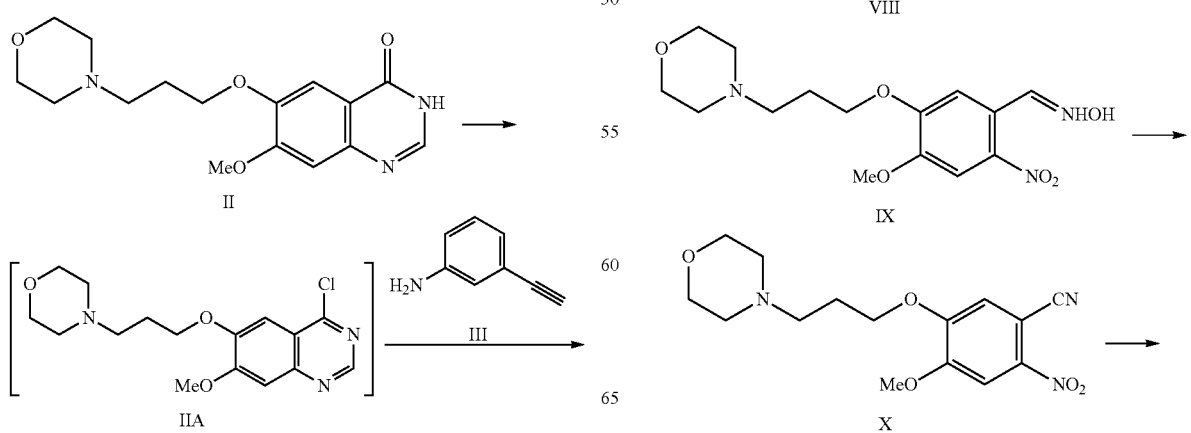

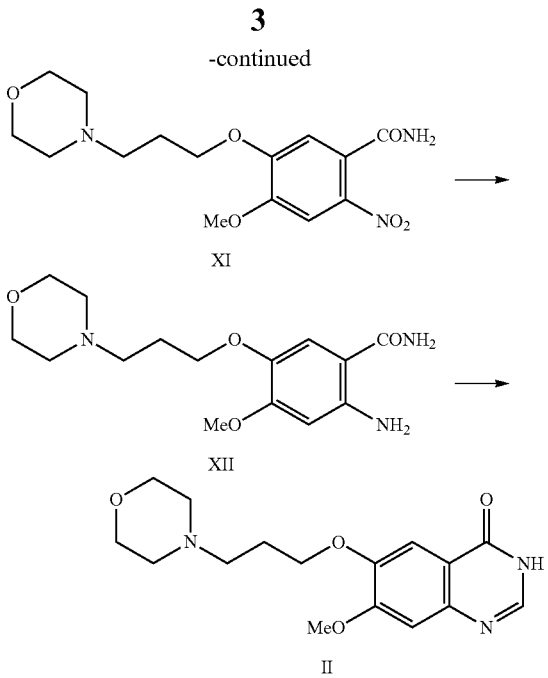

Process for preparing compound of formula-II has the following disadvantages.
a) Process for preparing compound of formula-II is not commercially viable as Isovanillin of formula-III is very expensive.
b) The isolated yields of intermediates of formula-VII, VIII, IX, X, XI, XII & II are moderate.
c) The overall yield of formula-I is only about 10%
d) Process demands corrosive reagents like nitric acid, hydrogen peroxide and pyrophoric catalyst like Raney Ni.
e) Process involves cumbersome work-up procedures

SUMMARY OF THE INVENTION

According to biological test reports, N—(3-ethynylphenyl)7-methoxy-6-(3-morpholinopropoxy) quinazolin-4-amine dihydrochloride of formula-I is found to be a promising small molecule having inhibitory effect against EGF-type receptor tyrosine kinase enzymes and Erb group receptors like Erb-2, Erb-3, and Erb-4 tyrosine kinase sensitive cancers.

Keeping in view of the difficulties in commercialization of the known process, we aimed to develop a simple, economically, environmentally friendly process for the commercial production of N—(3-ethynylphenyl)-7-methoxy-6-(3-morpholinopropoxy) quinazolin-4-amine dihydrochloride of formula-I.

The present invention provides an alternate & improved process for preparing compound of formula-I. In particular, the process according to the present invention provides improved yield of the compound of formula-I.

The main aspect of the present invention is to provide an improved process for the preparation of compound of formula-I by avoiding expensive reactants like Isovanillin in the process.

Another aspect of the present invention is to provide an improved process for the preparation of compound of formula-I by avoiding pyrophoric catalysts like Raney Nickel, high pressure reactions in the process.

Yet another aspect of the present invention is to provide an improved process for the preparation of compound of formula-I by avoiding cumbersome work-up procedures.

Yet another aspect of the present invention is to provide an improved process for the preparation of compound of formula-I by improving process timelines by avoiding isolation of intermediates wherever possible.

Yet another aspect of the present invention is to provide an improved process for the preparation of compound of formula-I with improved overall yield of compound of formula-I.

Accordingly, the main aspect of present invention for the preparation of compound of formula I, wherein present process uses readily and cheaply available 6, 7-dimethoxyquinazoline-4(3H)-one of formula-XIII as starting material to make the compound of formula-I. Compound of formula-XIII is commercially available or can be readily prepared from veratrole.

Accordingly, another aspect of the present invention is to provide a process for the preparation of compound of formula (I) comprising the steps of:
a) selective demethylation of 6, 7-dimethoxyquinazoline-4 (3H)-one of formula-XIII using DL-Methionine-sulfuric acid medium to get 6-hydroxy-7-methoxy quinazoline-4 (3H)-one of formula-XIV,
b) acetylation of 6-hydroxy-7-methoxyquinazoline-4(3H)-one of formula-XIV in acetic anhydride medium to get 6-acetoxy-7-methoxyquinazoline-4(3H)-one of formula-XV,
c) reacting 6-acetoxy-7-methoxy-quinazoline-4(3H)-one of formula-XV with thionyl chloride in the presence of DMF in chloroform to get 6-acetoxy-4-chloro-7-methoxyquinazoline hydrochloride of formula-XVI as in-situ intermediate,
d) reacting 6-acetoxy-4-chloro-7-methoxyquinazoline hydrochloride of formula-XVI in-situ with 3-ethynylaniline of formula-III in isopropanol medium to get 6-acetoxy-4-(3-ethynylanilino)-7-methoxyquinazoline hydrochloride of formula-XVII as in-situ intermediate,
e) treating 6-acetoxy-4-(3-ethynylanilino)-7-methoxyquinazoline hydrochloride salt of formula-XVII in-situ with aqueous ammonia in methanol medium to get 4-(3-ethynylanilino)-6-hydroxy-7-methoxyquinazoline of formula-XVIII,
f) reacting 4-(3-ethynylanilino)-6-hydroxy-7-methoxyquinazoline of formula-XVIII with 3-morpholinopropyl chloride of compound of formula-VI in presence of base in DMF to get N—(3-ethynylphenyl)-7-methoxy-6-(3-morpholinopropoxy) quinazolin-4-amine of formula-IV,
g) converting compound of formula-IV to its corresponding dihydrochloride salt of formula-I.

DETAILED DESCRIPTION OF THE PRESENT INVENTION

Schematic representation of the present invention is as given in scheme-3 below.

Scheme-3

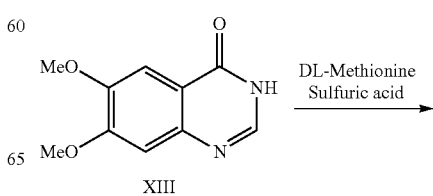

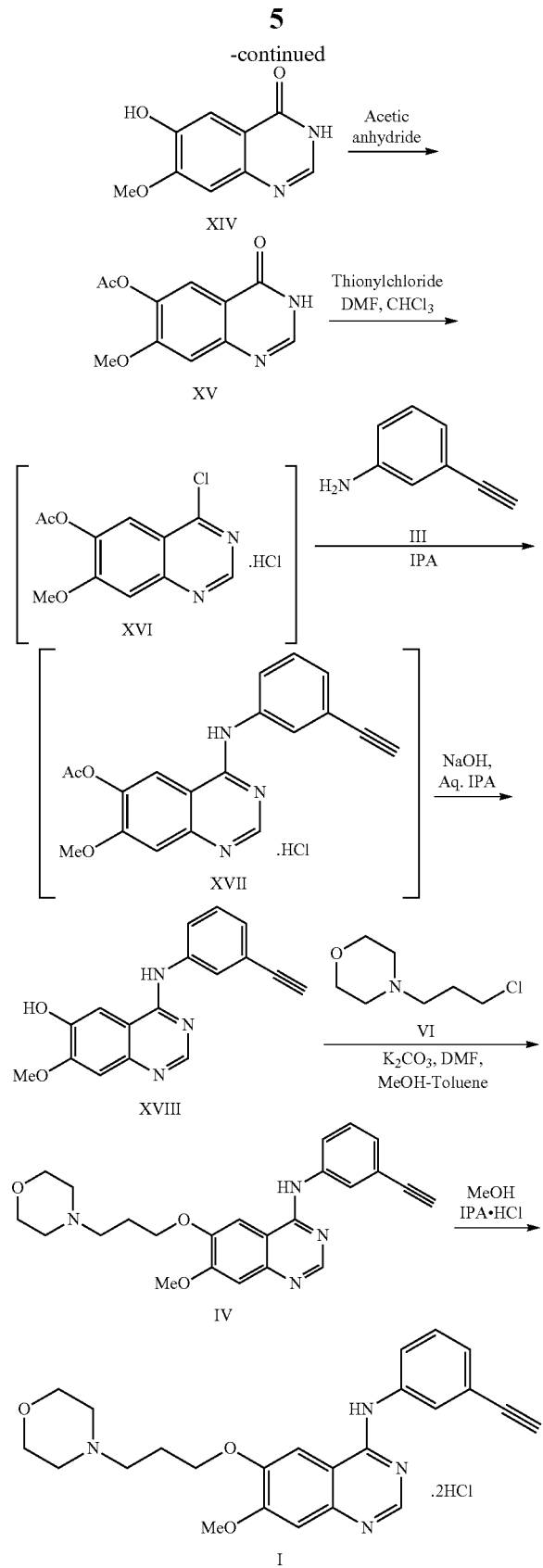

employed can be DL-Methionine-sulfuric acid mixture, D-Methionine-sulfuric acid mixture, L-Methionine-sulfuric acid mixture, aqueous hydrobromic acid or pyridine hydrochloride medium preferably DL-Methionine-sulfuric acid mixture. The temperatures at which de-methylation performed can be from 25-100° C., preferably at 90-95° C. After completion of reaction monitored by TLC, cooled the reaction mass to about room temperature and quenched in ice water and the pH is adjusted to about neutral point with aqueous base. Base is selected from aqueous ammonia, aqueous sodium hydroxide, aqueous potassium hydroxide or any other equivalent inorganic base preferably sodium hydroxide. After pH adjustment, the resulting product is filtered and dried to afford 6-hydroxy-7-methoxy-quinazoline-4(3H)-one of formula-XIV as crystalline solid. The yield is above >90%. The HPLC purity is >98%

According to the present invention, in step (ii), 6-hydroxy-7-methoxy-quinazoline-4(3H)-one of formula-XIV is protected using acylating agent in neat or in chlorinated solvent medium like methylene chloride or chloroform preferably methylene chloride. The acylating agent can be selected from acetic anhydride, acetyl chloride, or any other equivalent acid chloride preferably acetic anhydride. The elevated temperatures can be from 50-150° C., preferably at 120-125° C. After completion of reaction monitored by TLC, cooled the reaction mass to about room temperature and quenched in ice water. The resulting product is filtered and purified by crystallization from dimethylformamide to afford 6-acetoxy-7-methoxy-quinazoline-4(3H)-one of formula-XV as crystalline solid. The yield is above >75%. The HPLC purity is greater than 98%.

According to the present invention, in step (iii), 6-acetoxy-7-methoxy-quinazoline-4(3H)-one of formula-XV is being chlorinated with a chlorinating agent using catalyst in neat or in chlorinated solvent medium at 60-65° C. The chlorinating agent can be selected from oxalyl chloride, phosphorous oxychloride, thionyl chloride or any other equivalent chlorinating agent preferably thionyl chloride. The catalyst is selected from dimethylformamide or pyridine preferably dimethylformamide. The chlorinating solvent is selected from methylene chloride or chloroform preferably chloroform. After completion of reaction monitored by HPLC, the reaction mass is cooled to room temperature and quenched in aqueous base solution. The base is selected from sodium bicarbonate, potassium bicarbonate, sodium hydroxide, potassium hydroxide, sodium carbonate, potassium carbonate or any other equivalent inorganic base preferably sodium bicarbonate. The resulting organic layer is separated and distilled off solvent completely under vacuum and the resulting 6-acetoxy-4-chloro-7-methoxy-quinazoline hydrochloride of formula-XVI is isolated from isopropyl alcohol.

The wet product of formula-XVI is condensed further with 3-ethynylaniline of formula-III in isopropyl alcohol medium. The temperature at which the reaction is performed at room temperature or at reflux temperature preferably at reflux temperature. After completion of reaction monitored by HPLC, the reaction mixture is cooled to room temperature and filtered to afford 6-acetoxy-4-(3-ethynylanilino)-7-methoxyquinazoline hydrochloride of formula-XVII as crystalline solid. Thereafter the wet product of formula-XVII is hydrolyzed with aqueous base solution in aqueous alcohol medium at elevated temperature. The base is selected from potassium hydroxide or sodium hydroxide or any other equivalent inorganic base preferably sodium hydroxide. The alcohol is selected from methanol or isopropyl alcohol preferably isopropyl alcohol. The tempera- Accordingly, in step (i), selective demethylation of 6,7-dimethoxy-quinazoline-4(3H)-one of formula-XIII is achieved using de-methylating agent. De-methylating agent ture at which hydrolysis is carried out is in the range of 25-70° C. preferably at 40-50° C. After completion of reaction monitored by HPLC, the reaction mixture is cooled to room temperature and the pH adjusted to neutral point using dilute Hydrochloric acid. The resulting product is filtered, washed with DM water and dried to get 4-(3-ethynylanilino)-7-methoxy-quinazolin-6-ol of formula-XVIII as crystalline solid. The isolated yield of product of formula-XVIII is in the range of 75-80% from compound of formula-XV and HPLC purity is greater than 99%.

According to the present invention, in step (iv), 4-(3-ethynylanilino)-7-methoxy-quinazolin-6-ol of formula-XVIII is condensed with 3-morpholinopropyl chloride of formula-IV in potassium carbonate-DMF medium. The temperature at which the condensation is carried out is in the range of 20–100° C. preferably at 80-85° C. After completion of reaction monitored by HPLC, the reaction mass is cooled to room temperature and the salts are filtered. The filtrate is quenched in ice water followed by filtration and drying to afford N—(3-ethynylphenyl)-7-methoxy-6-(3-morpholinopropoxy)quinazolin-4-amine of formula-IV as crystalline solid. The product is further purified from an organic solvent or organic solvent mixture to afford pure compound of formula-IV. The isolated yield is in the range of 74-80% and the HPLC purity is greater than 99.9%.

According to the present invention, in step (v), N—(3-ethynylphenyl)-7-methoxy-6-(3-morpholinopropoxy)quinazolin-4-amine of formula-IV is converted to its corresponding dihydrochloride salt of formula-I using hydrochloric acid, dry hydrogen chloride gas dissolved in organic solvent. The organic solvent can be selected from methanol, isopropyl alcohol, ethanol, acetone, ethyl acetate or any other suitable organic solvent preferably isopropyl alcohol. After completion of salt formation, the product is filtered and washed with isopropyl alcohol to afford N—(3-ethynylphenyl)-7-methoxy-6-(3-morpholinopropoxy)quinazolin-4-amine dihydrochloride of formula-I as white crystalline solid. The isolated yield is above 85% and the HPLC purity is greater than 99.9%.

The isolated compound of formula-I is having the following physical characteristics.

FT-IR (KBr disc; λ, cm-1): 3406 (N—H str); 3063, 3000 (Aromatic —C—H str); 2943, 2838 (Aliphatic —C—H str); 2623 (br, due to HCl salt); 2100 (—C≡C— str); 1633 (—C=N— str); 1438 (N—H bending); 1282 (—C—N str); 1219, 1159, 1002 (—C—O str) $^1$HNMR (DMSO-d6; 400 MHz, δ ppm): 2.33-2.35 (m, 2H); 3.12 (br, m, 2H); 3.29-3.34 (br, m, 2H); 3.48-3.51 (br, m, 2H); 3.80-3.85 (m, 2H); 3.96-4.0 (m, 5H); 4.28 (s, 1H); 4.38-4.41 (t, 2H); 7.39-7.41 (m, 2H); 7.47-7.51 (t, 1H); 7.83-7.85 (d, 1H); 7.92 (m, 1H); 8.61 (m, 1H); 8.86 (s, 1H); 11.04 (s, 1H), 11.72 & 15.40 (br, s, 2H) $^{13}$CNMR (DMSO-d6; 100 MHz; δ ppm): 22.72, 15.10, 53.48, 56.49, 63.17, 67.28, 81.21, 82.94, 99.95, 105.64, 107.35, 121.90, 125.28, 127.54, 129.00, 129.17, 135.85, 137.33, 148.73, 148.93, 156.32, 158.13

Mass: 419.3 [M+H]$^+$

DSC: Peak observed at 279.55° C.

PXRD (2θ, °): 5.76, 6.76, 7.13, 7.64, 9.81, 12.62, 13.50, 13.97, 14.23, 15.27, 15.77, 17.22, 20.30, 20.60, 21.44, 22.42, 22.95, 24.81, 25.82, 27.37, 28.10, 28.53, 29.60, 30.75, 32.42, 34.15 (±0.2°)

According to the present invention, in step (vi), N—(3-ethynylphenyl)-7-methoxy-6-(3-morpholinopropoxy)quinazolin-4-amine dihydrochloride of formula-I is optionally purified by crystallization from an organic solvent or organic solvent mixture selected from methanol, ethanol, isopropyl alcohol, cyclohexane, toluene, n-heptane, methyl t-butyl ether, isopropyl ether or its mixture preferably methanol. The HPLC purity of N—(3-ethynylphenyl)-7-methoxy-6-(3-morpholinopropoxy) quinazolin-4-amine dihydrochloride of formula-I after isolation is greater than 99.9%. The isolated yield is above 90-95%.

Accordingly, the present invention provides an improved process for the preparation of N—(3-ethynylphenyl)-7-methoxy-6-(3-morpholinopropoxy)quinazolin-4-amine dihydrochloride of formula-I

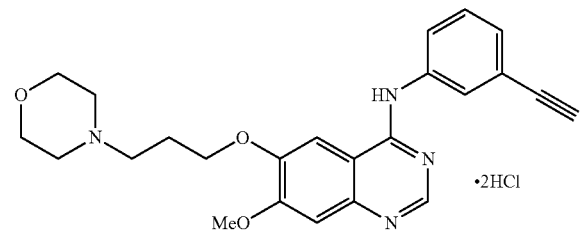

which comprises:—
(i) selective demethylation of 6,7-dimethoxy-quinazoline-4(3H)-one of formula-XIII

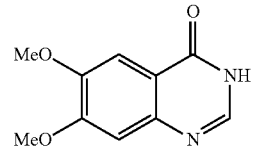

is achieved using de-methylating agent to get 6-hydroxy-7-methoxy-quinazoline-4(3H)-one of formula-XIV

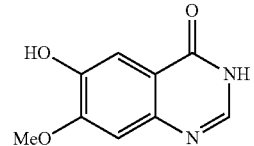

(ii) protecting 6-hydroxy-7-methoxy-quinazoline-4(3H)-one of formula-XIV using acylating agent to get 6-acetoxy-7-methoxy-quinazoline-4(3H)-one of formula-XV

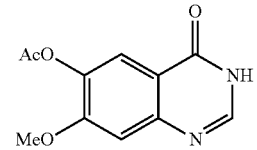

(iii) chlorination of 6-acetoxy-7-methoxy-quinazoline-4(3H)-one of formula-XV with chlorinating agent in the presence of catalyst in an organic solvent to get (4-chloro-7-methoxy-quinazolin-6-yl) acetate hydrochloride of compound of formula-XVI,

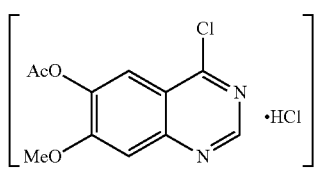

XVI which is reacted in-situ with 3-ethynylaniline of formula-III in alcoholic solvent medium to get [4-(3-ethynylanilino)-7-methoxy-quinazolin-6-yl] acetate hydrochloride of formula-XVII

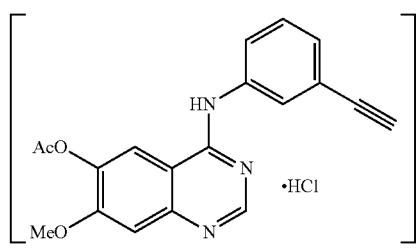

XVII which is further subjected to de-protection of acetoxy moiety using aqueous alcoholic medium to get 4-(3-ethynylanilino)-7-methoxy-quinazolin-6-ol of formula-XVIII

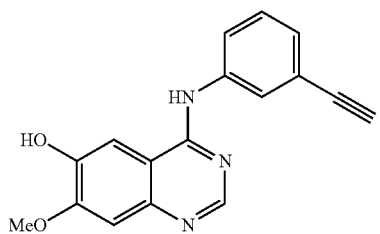

XVIII (iv) condensing 4-(3-ethynylanilino)-7-methoxy-quinazolin-6-ol of formula-XVIII with 3-morpholinopropyl chloride of formula-VI

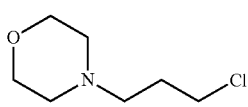

VI in dimethylformamide-potassium carbonate medium (any other medium will work for this reaction?) to get N—(3-ethynylphenyl)-7-methoxy-6-(3-morpholinopropoxy)quinazolin-4-amine of formula-IV

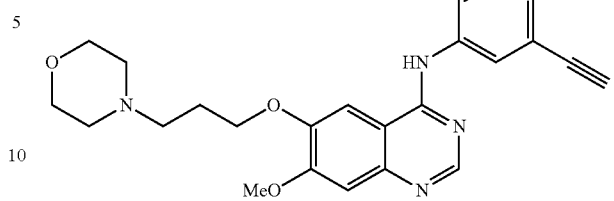

IV (v) converting N—(3-ethynylphenyl)-7-methoxy-6-(3-morpholinopropoxy) quinazolin-4-amine of formula-IV to dihydrochloride salt of formula-I using hydrochloric acid gas dissolved in organic solvent medium

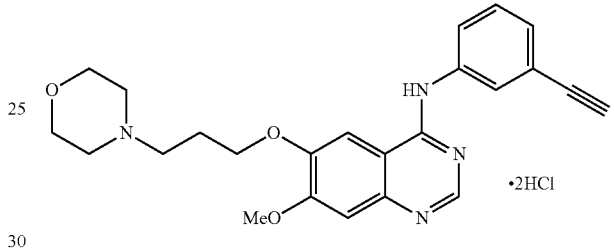

I (vi) optionally purification of N—(3-ethynylphenyl)-7-methoxy-6-(3-morpholinopropoxy) quinazolin-4-amine dihydrochloride of formula-I from alcoholic solvent or organic solvent mixture to remove impurities or residual solvents.

According to the present invention:

In step (i), selective demethylation of 6,7-dimethoxy-quinazoline-4(3H)-one of formula-XIII is achieved using de-methylating agent. De-methylating agent employed can be selected from DL-Methionine-sulfuric acid mixture, aqueous hydrobromic acid or pyridine hydrochloride medium preferably DL-Methionine-sulfuric acid mixture.

In step (i), the temperatures at which de-methylation performed can be from 25-100° C., preferably at 90-95° C.

In step (i), the pH is adjusted to about neutral point with aqueous base. Base can be selected from aqueous ammonia, aqueous sodium hydroxide, aqueous potassium hydroxide or any other equivalent inorganic base preferably sodium hydroxide.

The HPLC purity of 6-hydroxy-7-methoxy-quinazoline-4(3H)-one of formula-XIV in step (i) after isolation is >98%.

The yield of compound of formula-XIV in step (i) is >90%.

In step (ii) protection of 6-hydroxy-7-methoxy-quinazoline-4(3H)-one of formula-XIV is achieved using acylating agent in neat or in chlorinated solvent like methylene chloride or chloroform medium preferably methylene chloride. The acylating agent can be selected from acetic anhydride, acetyl chloride, or any other equivalent acylating agent preferably acetic anhydride.

The temperature at which the acylation in step (ii) can be performed is in the range of 0-150° C., preferably at 120-125° C.

Optionally in step (ii) 6-acetoxy-7-methoxy-quinazoline-4(3H)-one of formula-XV can be obtained by crystallization from dimethylformamide.

In step (ii), the HPLC purity of 6-acetoxy-7-methoxy-quinazoline-4(3H)-one of formula-XV after isolation is greater than 98%.

The yield of compound of formula-XV in step (ii) is in the range of 75-80%. In step (iii), chlorination of 6-acetoxy-7-methoxy-quinazoline-4(3H)-one of formula-XV is performed with chlorinating agent selected from oxalyl chloride, phosphorous oxychloride, thionyl chloride or any other equivalent chlorinating agent preferably thionyl chloride.

The catalyst used in chlorination of 6-acetoxy-7-methoxy-quinazoline-4(3H)-one of formula-XV in step (iii) is selected from dimethylformamide or pyridine preferably dimethylformamide.

The solvent in step (iii) is selected from methylene chloride or chloroform preferably chloroform.

The base employed in step (iii) during work-up is selected from sodium bicarbonate, potassium bicarbonate, sodium hydroxide, potassium hydroxide, sodium carbonate, potassium carbonate or any other equivalent inorganic base preferably sodium bicarbonate.

In step (iii) of the present invention, the wet product of (4-chloro-7-methoxy-quinazolin-6-yl) acetate hydrochloride of compound of formula-XVI is condensed further with 3-ethynylaniline of formula-III in isopropyl alcohol medium to get [4-(3-ethynylanilino)-7-methoxy-quinazolin-6-yl] acetate hydrochloride of formula-XVII.

The temperature at which the reaction is performed in step (iii) is at room temperature or at reflux temperature preferably at reflux temperature.

In step (iii) of the present invention, de-protection of [4-(3-ethynylanilino)-7-methoxy-quinazolin-6-yl] acetate hydrochloride of formula-XVII is performed with aqueous base solution wherein the base is selected from potassium hydroxide or sodium hydroxide or any other equivalent inorganic base preferably sodium hydroxide.

In step (iii), the organic solvent employed in de-protection of [4-(3-ethynylanilino)-7-methoxy-quinazolin-6-yl] acetate hydrochloride of formula-XVII is selected from methanol or isopropyl alcohol preferably isopropyl alcohol.

The temperature at which de-protection is carried out in step (iii) is in the range of 25-70° C. preferably at 40-50° C.

In step (iii), the HPLC purity of 4-(3-ethynylanilino)-7-methoxy-quinazolin-6-ol of formula-XVIII after isolation is in the range of 99-99.5%.

The yield of 4-(3-ethynylanilino)-7-methoxy-quinazolin-6-ol of formula-XVIII in step (iii) is in the range of 75-80%.

In step (iv) of the present invention, the base employed in the condensation step of 4-(3-ethynylanilino)-7-methoxy-quinazolin-6-ol of formula-XVIII with 3-morpholinopropyl chloride of formula-VI is potassium carbonate.

The solvent employed in step (iv) of the present invention in condensation of 4-(3-ethynylanilino)-7-methoxy-quinazolin-6-ol of formula-XVIII with 3-morpholinopropyl chloride of formula-VI is dimethylformamide.

In step (iv) of the present invention, the temperature at which condensation of 4-(3-ethynylanilino)-7-methoxy-quinazolin-6-ol of formula-XVIII with 3-morpholinopropyl chloride of formula-IV performed is in the range of 20-100° C. preferably at 80-85° C.

In step (iv) of the present invention, purification the resulting N—(3-ethynylphenyl)-7-methoxy-6-(3-morpholinopropoxy)quinazolin-4-amine of formula-IV by crystallization is selected from an organic solvent or organic solvent mixture selected from methanol, ethanol, isopropyl alcohol, cyclohexane, toluene, n-heptane, methyl t-butyl ether, isopropyl ether or its mixture.

In step (iv), the HPLC purity of N—(3-ethynylphenyl)-7-methoxy-6-(3-morpholinopropoxy) quinazolin-4-amine of formula-IV after isolation is greater than 99.9%.

The yield of N—(3-ethynylphenyl)-7-methoxy-6-(3-morpholinopropoxy)quinazolin-4-amine of formula-IV in step (iv) is in the range of 74-80%.

In step (v) of the present invention, N—(3-ethynylphenyl)-7-methoxy-6-(3-morpholino propoxy)quinazolin-4-amine of formula-IV is optionally converted to N—(3-ethynylphenyl)-7-methoxy-6-(3-morpholinopropoxy) quinazolin-4-amine dihydrochloride of formula-I using hydrochloric acid, dry hydrochloric acid gas dissolved in methanol, ethanol or isopropyl alcohol, acetone, ethylacetate or any other suitable organic solvent preferably hydrochloric acid gas dissolved in isopropyl alcohol.

In step (v) of the present invention, the organic solvent employed for hydrochloride salt formation is selected from methanol, ethanol or isopropyl alcohol preferably methanol.

In step (v), the HPLC purity of N—(3-ethynylphenyl)-7-methoxy-6-(3-morpholinopropoxy) quinazolin-4-amine dihydrochloride of formula-I after isolation is greater than 99.9%.

The yield of N—(3-ethynylphenyl)-7-methoxy-6-(3-morpholinopropoxy) quinazolin-4-amine dihydrochloride of formula-I in step (v) is above 85.0%.

The isolated product of N—(3-ethynylphenyl)-7-methoxy-6-(3-morpholinopropoxy) quinazolin-4-amine dihydrochloride of formula-I in step (vi) is having following physical characteristics.

FT-IR ($\lambda$, cm-1): 3406 (N—H str); 3063, 3000 (Aromatic —C—H str); 2943, 2838 (Aliphatic —C—H str); 2623 (br, due to HCl salt); 2100 (—C≡— str); 1633 (—C=N— str); 1438 (N—H bending); 1282 (—C—N str); 1219, 1159, 1002 (—C—O str) 1HNMR (DMSO-d6; 400 MHz, $\delta$ ppm): 2.33-2.35 (m, 2H); 3.12 (br, m, 2H); 3.29-3.34 (br, m, 2H); 3.48-3.51 (br, m, 2H); 3.80-3.85 (m, 2H); 3.96-4.0 (m, 5H); 4.28 (s, 1H), 4.38-4.41 (t, 2H); 7.39-7.41 (m, 2H); 7.47-7.51 (t, 1H); 7.83-7.85 (d, 1H); 7.92 (m, 1H); 8.61 (m, 1H); 8.86 (s, 1H); 11.04 (s, 1H), 11.72 & 15.40 (br, s, 2H) $^{13}$CNMR (DMSO-d6; 100 MHz; $\delta$ ppm): 22.72, 15.10, 53.48, 56.49, 63.17, 67.28, 81.21, 82.94, 99.95, 105.64, 107.35, 121.90, 125.28, 127.54, 129.00, 129.17, 135.85, 137.33, 148.73, 148.93, 156.32, 158.13

DSC: Peak observed at 279.55° C.

PXRD (2$\theta$, °): 5.76, 6.76, 7.13, 7.64, 9.81, 12.62, 13.50, 13.97, 14.23, 15.27, 15.77, 17.22, 20.30, 20.60, 21.44, 22.42, 22.95, 24.81, 25.82, 27.37, 28.10, 28.53, 29.60, 30.75, 32.42, 34.15 (±0.2°)

In step (vi) of the present invention, optionally purification N—(3-ethynylphenyl)-7-methoxy-6-(3-morpholinopropoxy) quinazolin-4-amine dihydrochloride of formula-I by crystallization is selected from an organic solvent or organic solvent mixture selected from methanol, ethanol, isopropyl alcohol, cyclohexane, toluene, n-heptane, methyl t-butyl ether, isopropyl ether or its mixture preferably methanol. In step (vi), the HPLC purity of N—(3-ethynylphenyl)-7-methoxy-6-(3-morpholinopropoxy) quinazolin-4-amine dihydrochloride of formula-I after isolation is greater than 99.9%.

The yield of N—(3-ethynylphenyl)-7-methoxy-6-(3-morpholinopropoxy) quinazolin-4-amine dihydrochloride of formula-I in step (vi) is in the range of 90-95%.

Advantages of Present Invention

1. The present invention provides an improved process for the preparation and isolation of highly pure N—(3-ethynylphenyl)-7-methoxy-6-(3-morpholinopropoxy) quinazolin-4-amine dihydrochloride of formula-I.
2. Present process produces N—(3-ethynylphenyl)-7-methoxy-6-(3-morpholinopropoxy) quinazolin-4-amine dihydrochloride of formula-I with >99.9% HPLC purity.
3. Present process avoids usage of expensive reactants and reagents.
4. Present process avoids usage of pyrophoric catalysts and high pressure reactions.
5. Present process improve the process timelines by avoiding isolation of intermediates.
6. Present process avoids cumbersome work-up procedures.
7. Present process achieves overall yield of 33%.
8. Present process is feasible on large scale production.
9. Present process is cost effective
10. Raw materials used in the process are commercially available.

BRIEF DESCRIPTION OF DRAWINGS

FIG. 2: Differential scanning calorimetry (DSC) of N—(3-ethynylphenyl)-7-methoxy-6-(3-morpholinopropoxy) quinazolin-4-amine dihydrochloride of formula-I.

Figure 1:
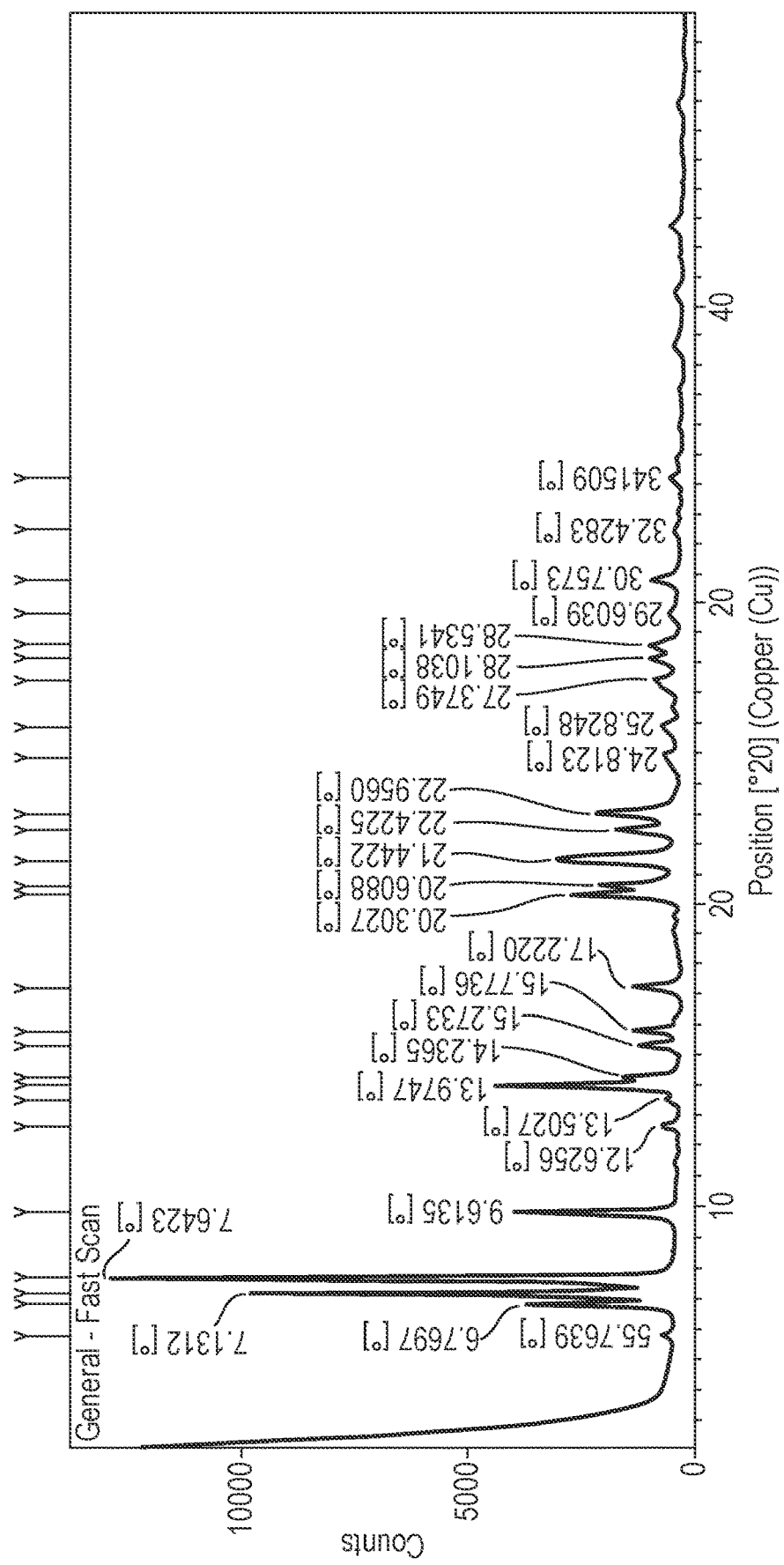
FIG. 1: Powder X-ray diffraction of N—(3-ethynylphenyl)-7-methoxy-6-(3-morpholinopropoxy) quinazolin-4-amine dihydrochloride of formula-I.

Having thus described the present invention with reference to certain preferred embodiments, the invention is further illustrated by the examples, which follow.

The following examples are provided for illustrative purpose only and are not intended to limit the scope of invention in anyway.

Example-1

Preparation of N—(3-ethynylphenyl)-7-methoxy-6-(3-morpholinopropoxy)quinazolin-4-amine Dihydrochloride of Formula-I Stage-1: Preparation of 6-hydroxy-7-methoxy-quinazoline-4(3H)-one of Formula-XIV Into a reaction flask, concentrated sulfuric acid (607.2 g; 25.5 m. eq), 6,7-dimethoxy-quinazoline-4(3H)-one of formula-XI (50 g; 1.0 m. eq) and DL-Methionine (41.5 g; 1.15 m. eq) were sequentially added under stirring. The reaction mass was heated to 90-95° C. and maintained for about 6 h. The progress of the reaction was monitored by TLC. After completion of the reaction, cooled the reaction mass to 25-35° C. and quenched by adding ice-flakes (~1300 g) at 25-35° C. and stirred for 1 h. The resulting product was filtered and suspended the wet product in DM water (800 mL). The pH of the reaction mixture was adjusted to about 7.5 with lye solution. The product was filtered, washed with DM water and dried at 70-75° C. to afford 6-hydroxy-7-methoxy-quinazoline-4(3H)-one of formula-XIV (41.0 g; 90.0% by theory).
HPLC purity: >98%

Stage-2: Preparation of 6-acetoxy-7-methoxy-quinazoline-4(3H)-one of Formula-XV

Into a reaction flask, acetic anhydride (864 g, 16.25 m. eq) followed by 6-hydroxy-7-methoxy-quinazoline-4(3H)-one of formula-XII (100 g; 1.0 m. eq) were added under stirring and heated the reaction mass to 120-125° C. and maintained for about 3 h. The progress of the reaction was monitored by TLC. After completion of reaction, cooled the reaction mass to 25-35° C. and quenched in ice water (2000 g) under stirring. The resulting product mixture was heated to 60-65° C., maintained for 1 h and cooled the reaction mass to 25-35° C. and maintained under stirring for 2 h. The resulting product was isolated by filtration and washed with water. The product was further purified by recrystallization from dimethylformamide to afford 6-acetoxy-7-methoxy-quinazoline-4(3H)-one of formula-XV as crystalline solid (90.0 g; 75% by theory).
HPLC purity: >98%

Stage-3: Preparation of 4-(3-ethynylanilino)-7-methoxy-quinazolin-6-ol of Formula-XVII i) Preparation of (4-chloro-7-methoxy-quinazolin-6-yl) Acetate HCl (XVI)

Into a reaction flask, chloroform (2100 mL), 6-acetoxy-7-methoxy-quinazoline-4(3H)-one of formula-XV (150.0 g; 1.0 m. eq) and dimethyl formamide (45 g; 0.96 m. eq) were added under stirring. To this, thionyl chloride (114.3 g; 1.5 m. eq) was added dropwise at 25-35° C. After addition, heated the reaction mass to reflux temperature and maintained for about 5 h. The progress of the reaction was monitored by HPLC. After completion of reaction, reaction mixture was quenched with aqueous sodium bicarbonate solution under stirring and the resultant organic layer was separated. The organic layer was dried over anhydrous sodium sulfate and filtered. The filtrate was evaporated under reduced pressure to afford (4-chloro-7-methoxy-quinazolin-6-yl) acetate hydrochloride of compound of formula-XVI as pale yellow color wet solid. The wet product was purified by trituration with isopropyl alcohol, filtered and the wet solid (~280 g) was used as such in the next stage without further drying. HPLC purity: >95.0% ii) Preparation of [4-(3-ethynylanilino)-7-methoxy-quinazolin-6-yl] acetate Hydrochloride of Formula-XVII Into a reaction flask, the above wet product of formula-XVI (~280 g) was suspended in isopropyl alcohol (4200 mL) and condensed with 3-ethynylaniline of formula-III (65.7 g; 1.15 m. eq against of formula-XV) and heated to reflux temperature. The reaction mass was maintained under stirring for about 3 h. Progress of the reaction was monitored by HPLC. After completion of reaction, cooled the reaction mass to ambient temperature and filtered. The wet product (~230 g) of [4-(3-ethynylanilino)-7-methoxy-quinazolin-6-yl] acetate hydrochloride of formula-XVII was used in the next stage without drying.
HPLC purity: >99.0% iii) Preparation of 4-(3-ethynylanilino)-7-methoxy-quinazolin-6-ol of Formula-XVIII Into a reaction flask, 20% v/v aqueous isopropyl alcohol (2.25 L) followed by sodium hydroxide (76.85 g, 3.0 m. eq against of formula-XV). To the resulting solution, [4-(3-ethynylanilino)-7-methoxy-quinazolin-6-yl] acetate hydrochloride of formula-XVII (~230 g) was added and heated to 45-50° C. and maintained under stirring for about 3 h. Progress of the reaction was monitored by HPLC. After completion of reaction, cooled the reaction mass to ambient temperature and the pH was adjusted to about 7 with dil. HCl. The resulting precipitate was filtered, washed with water and dried at 65-75° C. to get of 4-(3-ethynylanilino)-7-methoxy-quinazolin-6-ol of formula-XVIII (143.0 g; 77.0% by theory based on formula-XV)

HPLC purity: >99%.

Stage-4: Preparation of N—(3-ethynylphenyl)-7-methoxy-6-(3-morpholinopropoxy) quinazolin-4-amine of Formula-IV Into a reaction flask, dimethylformamide (460 mL) followed by potassium carbonate (62.7 g; 1.15 m. eq), 4-(3-ethynylanilino)-7-methoxy-quinazolin-6-ol of formula-XVIII (115.0 g; 1.0 m. eq) and 3-morpholinopropyl chloride of compound of formula-VI (73.7 g; 1.14 m. eq) were added. The resulting suspension was heated and maintained at 80-85° C. for about 3 h. Progress of the reaction was monitored by HPLC. After completion of reaction, cooled the reaction mass to ambient temperature and filtered. The filtrate was quenched with water (~1700 mL) at ambient temperature under stirring and the resulting product was filtered and washed with water followed by isopropyl alcohol to afford compound of formula-IV (~160 g, wet product) as white solid. The compound was purified further by crystallization from toluene-methanol mixture to afford 123 g (74.6% by theory) of N—(3-ethynylphenyl)-7-methoxy-6-(3-morpholinopropoxy)quinazolin-4-amine of formula-IV as crystalline solid.

HPLC Purity: 99.9%

Stage-5: Preparation of N—(3-ethynylphenyl)-7-methoxy-6-(3-morpholinopropoxy)-quinazolin-4-amine Dihydrochloride of Formula-I Into a reaction flask, methanol (2.025 L) followed by 90 g of N—(3-ethynylphenyl)-7-methoxy-6-(3-morpholinopropoxy)quinazolin-4-amine of formula-IV were added and heated to dissolve at 50-55° C. After complete dissolution, the solution was clarified with activated carbon and filtered. The filtrate was heated in a clean reaction flask to 50-55° C. and was added IPA·HCl (~131 g; 2.25 m. eq) under stirring. The resulting thick precipitate was maintained under stirring at reflux temperature for about 4 h and cooled to ambient temperature. The precipitate was filtered, washed with methanol and dried at 60-65° C. to get N—(3-ethynylphenyl)-7-methoxy-6-(3-morpholinopropoxy)-quinazolin-4-amine dihydrochloride of formula-I (91.4 g; 86.5% by theory) as white crystalline solid.

HPLC purity: >99.9%

We claim:

1. A process for the preparation of N—(3-ethynylphenyl)-7-methoxy-6-(3-morpholinopropoxy)quinazolin-4-amine dihydrochloride salt of formula-I comprising the steps of:

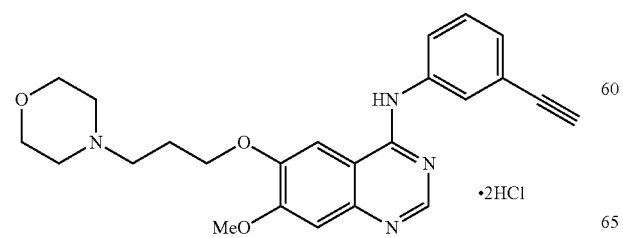

i) selective demethylation of 6,7-dimethoxy-quinazoline-4(3H)-one of formula-XIII

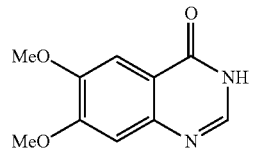

using a de-methylating agent to get 6-hydroxy-7-methoxy-quinazoline-4(3H)-one of formula-XIV,

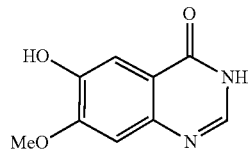

ii) converting 6-hydroxy-7-methoxy-quinazoline-4(3H)-one of formula-XIV to 4-(3-ethynylanilino)-7-methoxy-quinazolin-6-ol of formula-XVIII,

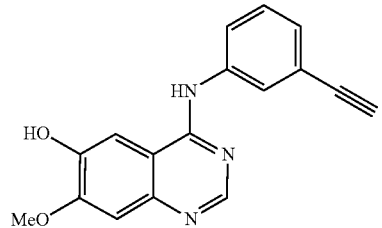

iii) condensing 4-(3-ethynylanilino)-7-methoxy-quinazolin-6-ol of formula-XVIII with 3-morpholinopropyl chloride of formula-VI,

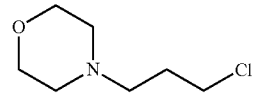

in dimethylformamide-potassium carbonate medium to get N—(3-ethynylphenyl)-7-methoxy-6-(3-morpholinopropoxy)quinazolin-4-amine of formula-IV,

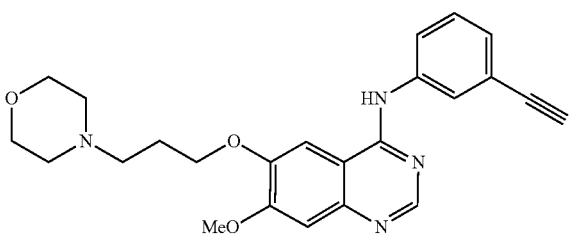

iv) converting N—(3-ethynylphenyl)-7-methoxy-6-(3-morpholinopropoxy) quinazolin-4-amine of formula-IV to N—(3-ethynylphenyl)-7-methoxy-6-(3-morpholinopropoxy)quinazolin-4-amine dihydrochloride salt of formula-I using hydrochloric acid or hydrochloric acid gas dissolved in organic solvent medium.

2. The process according to claim 1, wherein, in step (i):

(a) the de-methylating agent employed is selected from the group consisting of DL-Methionine-sulfuric acid mixture, aqueous hydrobromic acid and a pyridine hydrochloride medium, (b) the temperature at which de-methylation is performed is from 25-100° C., and (c) a base selected from the group consisting of aqueous ammonia, aqueous sodium hydroxide, aqueous potassium hydroxide, and equivalent inorganic bases is employed.

3. The process according to claim 1, wherein, in step (iii), (a) potassium carbonate is employed in the condensation step, (b) dimethylformamide is employed in the condensation step, (c) the temperature at which the condensation is performed is in the range of 20-100° C. preferably at 60-70° C., (d) purification of the resulting N—(3-ethynylphenyl)-7-methoxy-6-(3-morpholinopropoxy)quinazolin-4-amine of formula-IV by crystallization is conducted using methanol, ethanol, isopropyl alcohol, cyclohexane, toluene, n-heptane, methyl t-butyl ether, isopropyl ether, or mixtures thereof.

4. The process according to claim 1, wherein, in step (iv), (a) the conversion step is conducted using hydrochloric acid or dry hydrochloric acid gas dissolved in methanol, ethanol, isopropyl alcohol, acetone, or ethylacetate, (b) the organic solvent medium employed for dihydrochloride salt formation is selected from the group consisting of methanol, ethanol, and isopropyl alcohol, (c) the isolated product of N—(3-ethynylphenyl)-7-methoxy-6-(3-morpholinopropoxy) quinazolin-4-amine dihydrochloride of formula-I is characterized by:

(1) FT-IR (λ, cm-1): 3406 (N—H str); 3063, 3000 (Aromatic —C—H str); 2943, 2838 (Aliphatic —C—H str); 2623 (br, due to HCl salt); 2100 (—C≡C— str); 1633 (—C═N— str); 1438 (N—H bending); 1282 (—C—N str); 1219, 1159, 1002 (—C—O str)

(2)¹HNMR (DMSO-d6; 400 MHz, δ ppm): 2.33-2.35 (m, 2H); 3.12 (br, m, 2H); 3.29-3.34 (br, m, 2H); 3.48-3.51 (br, m, 2H); 3.80-3.85 (m, 2H); 3.96-4.0 (m, 5H); 4.28 (s, 1H), 4.38-4.41 (t, 2H); 7.39-7.41 (m, 2H); 7.47-7.51 (t, 1H); 7.83-7.85 (d, 1H); 7.92 (m, 1H); 8.61 (m, 1H); 8.86 (s, 1H); 11.04 (s, 1H), 11.72 & 15.40 (br, s, 2H)

(3)¹³CNMR (DMSO-d6; 100 MHz; δ ppm): 22.72, 15.10, 53.48, 56.49, 63.17, 67.28, 81.21, 82.94, 99.95, 105.64, 107.35, 121.90, 125.28, 127.54, 129.00, 129.17, 135.85, 137.33, 148.73, 148.93, 156.32, 158.13

(4) DSC: Peak observed at 279.55° C.

(5) PXRD (2θ, °): 5.76, 6.76, 7.13, 7.64, 9.81, 12.62, 13.50, 13.97, 14.23, 15.27, 15.77, 17.22, 20.30, 20.60, 21.44, 22.42, 22.95, 24.81, 25.82, 27.37, 28.10, 28.53, 29.60, 30.75, 32.42, 34.15)(±0.2°).

5. The process according to claim 1, further comprising the step of:

v) purification of N—(3-ethynylphenyl)-7-methoxy-6-(3-morpholinopropoxy) quinazolin-4-amine dihydrochloride of formula-I from alcoholic solvent or organic solvent mixture.

6. The process according to claim 5, wherein, in step (v), the purification is by crystallization from an organic solvent or organic solvent mixture selected from the group consisting of methanol, ethanol, isopropyl alcohol, cyclohexane, toluene, n-heptane, methyl t-butyl ether, isopropyl ether, and mixtures thereof.

7. The process according to claim 1, wherein, in step ii, converting 6-hydroxy-7-methoxy-quinazoline-4(3H)-one of formula-XIV to 4-(3-ethynylanilino)-7-methoxy-quinazolin-6-ol of formula-XVIII comprises:

ii-a) protecting the 6-hydroxy-7-methoxy-quinazoline-4(3H)-one of formula-XIV using an acylating agent to get 6-acetoxy-7-methoxy-quinazoline-4(3H)-one of formula-XV,

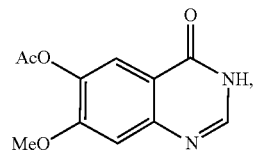

XV and ii-b) chlorination of 6-acetoxy-7-methoxy-quinazoline-4(3H)-one of formula-XV with a chlorinating agent in the presence of a catalyst in an organic solvent to get (4-chloro-7-methoxy-quinazolin-6-yl) acetate hydrochloride of compound of formula-XVI,

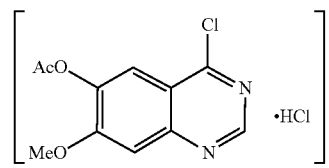

XVI which is reacted in-situ with 3-ethynylaniline in an alcoholic solvent medium to get [4-(3-ethynylanilino)-7-methoxy-quinazolin-6-yl] acetate hydrochloride of formula-XVII,

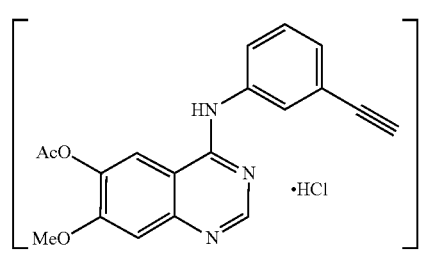

XVII which is further subjected to de-protection of acetoxy moiety using aqueous alcoholic medium to get 4-(3-ethynylanilino)-7-methoxy-quinazolin-6-ol of formula-XVIII.

8. The process according to claim 7, wherein, in step (ii-a),
- (a) the acylating agent is selected from the group consisting of acetic anhydride and acetyl chloride,
- (b) an organic solvent selected from the group consisting of methylene chloride and chloroform medium is employed,
- (c) the temperature at which the acylation is performed is in the range of 0-150° C.,
- (d) optionally 6-acetoxy-7-methoxy-quinazoline-4(3H)-one of formula-XV is obtained by crystallization from dimethylformamide.

9. The process according to claim 7, wherein, in step (ii-b),
- (a) the chlorinating agent is selected from the group consisting of oxalyl chloride, phosphorous oxychloride, and thionyl chloride,
- (b) the catalyst is selected from the group consisting of dimethylformamide and pyridine,
- (c) the organic solvent is selected from the group consisting of methylene chloride and chloroform,
- (d) a base selected from the group consisting of sodium bicarbonate, potassium bicarbonate, sodium hydroxide, potassium hydroxide, sodium carbonate, and potassium carbonate is employed during work-up,
- (e) wet compound of formula-XVI is condensed with 3-ethynylaniline in isopropyl alcohol medium to get [4-(3-ethynylanilino)-7-methoxy-quinazolin-6-yl] acetate hydrochloride of formula-XVII,
- (f) the temperature at which the condensation is performed is at room temperature or at reflux temperature,
- (g) de-protection of the acetoxy moiety is performed with an aqueous base solution wherein the base is selected from the group consisting of potassium hydroxide and sodium hydroxide,
- (h) the aqueous alcoholic medium employed in de-protection of [4-(3-ethynylanilino)-7-methoxy-quinazolin-6-yl] acetate hydrochloride of formula-XVII comprises methanol or isopropyl alcohol,
- (i) the temperature at which de-protection is carried out is in the range of 25-70° C. preferably at 40-50° C.

* * * * *